United States Patent [19]

Kida et al.

[11] 4,452,891

[45] Jun. 5, 1984

[54] METHOD FOR PRODUCTION OF MYCOPHENOLIC ACID BY FERMENTATION

[75] Inventors: Takao Kida, Yokosuka; Takehiko Ishikawa, Kawasaki; Hiroshiro Shibai, Chigasaki, all of Japan

[73] Assignee: Ajinomoto Company Incorporated, Tokyo, Japan

[21] Appl. No.: 300,041

[22] Filed: Sep. 8, 1981

[30] Foreign Application Priority Data

Sep. 8, 1980 [JP] Japan ............................. 55-124380
Sep. 8, 1980 [JP] Japan ............................. 55-124381

[51] Int. Cl.³ .................... C12P 17/04; C12P 17/02; C12N 15/00; C12R 1/81
[52] U.S. Cl. ................................ 435/126; 435/123; 435/172.1; 435/934; 735/68
[58] Field of Search ............... 435/123, 126, 933, 934, 435/172

[56] References Cited

U.S. PATENT DOCUMENTS 4,115,197 9/1978 Queener et al. .................... 435/123

FOREIGN PATENT DOCUMENTS 55-19055 2/1980 Japan .................................. 435/126

OTHER PUBLICATIONS

Birch, "Biosynthesis of some Monobenzenoid Quinones" Ciba Foundation Symposium, Quinones Electron Transport 1960 pp. 233-243 Chem. Abstracts 56: 9220i.

Cohen et al, "Effects of Clofibrate on Sterol Metabolism in the Rat" Biochemica et Biophysica Acta 369 (1974) pp. 79-85.

Andressen et al, "Nicotinamide-Adenine Dinucleotide Phosphate Dependant Formate Kehydrogenase from Clostridium Thermoaceticum" Journal of Bacteriology 120(1) (1974) pp. 6-14 Chemical Abstracts 81: 165365h.

Van Dijk et al, "Purification and Properties of Hydrogenase from Megasphaera Elsdenii" European Journal of Biochemistry 102(2) (1979) pp. 317-330 Chem. Abstracts 92: 89805m.

*Primary Examiner*—Thomas G. Wiseman
*Assistant Examiner*—John E. Tarcza
*Attorney, Agent, or Firm*—Oblon, Fisher, Spivak, McClelland & Maier

[57] ABSTRACT

Mycophenolic acid is produced by aerobically culturing in a culture medium a mutant of the genus Penicillium capable of producing mycophenolic acid, said mutant being resistant to clofibrat, and recovering the mycophenolic acid which accumulates in the culture medium.

1 Claim, No Drawings

METHOD FOR PRODUCTION OF MYCOPHENOLIC ACID BY FERMENTATION

BACKGROUND OF THE INVENTION

1. Field of the Invention

The present invention relates to a method for producing mycophenolic acid by fermentation.

2. Description of the Prior Art

Mycophenolic acid (hereinafter referred to as MPA) is a compound with several useful biological properties such as antiviral and antitumor activities (K. Ando et al., *J. Antibiot*, 21, 649-652, 1968 and R. H. Williams et al., *J. Antibiot*, 21, 463-464, 1968).

It has also been reported that MPA has antimicrobial activity (K. Gilliver, *Ann. Bot.* (London) 10, 271-282, 1946). MPA was initially isolated from a culture of a fungus belonging to the genus Penicillium and it is known that MPA is produced by many species of the genus Penicillium. For example, *P. brevi-compactum, P. stroniferum, P. scabrum, P. nagemi, P. Szaferi* and *P. patus-mai*, (*Biochem. J.* 27, 654, 1933). Recently, it has shown that a mutant of the genus Penicillium resistant to polyen- antibiotics produces more MPA than a parent strain (Japanese Published Unexamined Patent Application No. 115880/1978). A need, however, continues to exist for an improved technique of producing MPA in large quantities by a commercially acceptable technique.

SUMMARY OF THE INVENTION

Accordingly, one object of the present invention is to provide a means of producing MPA in large quantities from a mutant strain of an organism capable of producing MPA.

Briefly, this object and other objects of the present invention as hereinafter will become more readily apparent can be attained by a method of producing mycophenolic acid by fermentation by aerobically culturing in a culture medium a mutant of the genus Penicillium capable of producing mycophenolic acid, said mutant being resistant to clofibrat and recovering the mycophenolic acid product which accumulates in the culture medium.

DETAILED DESCRIPTION OF THE PREFERRED EMBODIMENTS

It has now been found that productivity of MPA can be significantly increased when resistance is imparted to a known MPA-producing strain of the genus Penicillium to the chemical agent "clofibrat". It has also been found that a mutant resistant to clofibrat and viologen dye, or clofibrat and alkyltrimethyl ammonium chloride produces much more MPA than the parent strain.

The microorganism employed in the present invention is a mutant resistant to clofibrat and is induced from a fungus of the genus Pencillium capable of producing MPA. In a preferred embodiment of the present invention, a mutant resistant to clofibrat and viologen dye, or clorfibrat and alkyltrimethyl ammonium chloride is preferably used.

A mutant of the invention may be induced from parent strains of the genus Penicillium capable of producing MPA by any conventional mutation method. The first step of the procedure of obtaining a mutant of the present invention is to mutate conidia (spores) of a parent strain with a suitable chemical mutagen such as N-methyl-N'-nitro-N-nitroso-guanidine (NG), nitrous acid or ethylmethanesulfonate, or with irradiation by ultraviolet light. When a chemicl mutagen is used, the treated cells should be washed to free the cells from the mutagen. The treated cells are then cultured on plates of a nutrient agar medium containing an amount of clofibrat which inhibits the growth of the parent strain until colonies are formed on the plates. Thereafter, the colonies which appear on the agar plate are picked-up as clofibrat-resistant mutants and the mutants are evaluated for MPA production according to a standard procedure. From among these mutants, a higher MPA-producing strain can be obtained with high frequency.

In order to obtain a preferred mutant additionally resistant to viologen dye or alkyltrimethyl ammonium chloride, a resistance to the chemical is imparted to the mutant resistant to clofibrat thus obtained in the same manner except that a plate of an agar medium containing viologen dye or alkyltrimethyl ammonium chloride is used instead of a plate containing clofibrat.

Any parent strain of fungus of the genus Penicillium capable of producing MPA can be used in the present invention. Suitable examples include *Penicillium brevi-compactum* QM8406 (ATCC 16024), *Penicillium stroniferum* ATCC 10111, *Penicillium stroniferum* NRRL 859 and the like.

Clofibrat utilized in the present invention is a chemotherapeutic agent conventionally used as an anticholesteremic agent and has the structure:

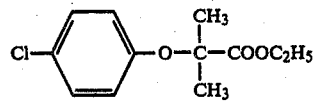

The compound exerts a toxic effect on fungi by inhibiting the enzyme activity which catalyzes the biosynthesis of mevalonic acid from 3-(hydroxy)-3-methylglutaryl-Co.A in the fatty acid biosynthetic pathway.

Viologen dye utilized in the present invention is a chemical agent having the following formula

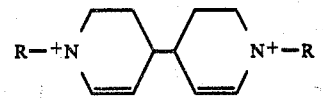

wherein R is methyl, ethyl, or benzyl. Methyl viologen dye is preferably used.

The alkyltrimethyl ammonium chloride compound utilized in the present invention is a cationic quaternary ammonium salt and is a surface-active agent. Suitable such salts preferably include dodecatrimethyl ammonium chloride and lauryltrimethyl ammonium chloride.

The preferred amounts of clofibrat, alkyltrimethyl chloride and viologen dye utilized in the nutrient agar medium are 500–2,000 mcg/ml, 10–500 mcg/ml, and 50–500 mcg/ml, respectively.

The product mutant strains of the present invention are those which can grow in a nutrient culture medium containing an amount of one of the chemicals stated above which is more than 1.2 times the minimum inhibitory concentration of the chemical to the parent strain. The mutant strains obtained produce more MPA than the parent strain. Product mutant strains include the following:

*Penicillium brevi-compactum* AJ 117090 FERM-BP-53 (Clofibrat$^r$)

*Penicillium brevi-compactum* AJ 117094 FERM-BP-54 (Clofibrat$^r$, MV$^r$)

*Penicillium brevi-compactum* AJ 117096 FERM-BP-55 Clofibratz$^r$, DTAC$^r$,

Clofibrat$^r$: resistance to clofibrat

MV$^r$: resistance to methylviologen

DTAC$^r$: resistance to dodecatrimethyl ammonium chloride.

The mutants identified by FERM-P numbers have been deposited with the Fermentation Research Institute, Agency of Industrial Science and Technology, Ministry of International Trade and Industry (FRI), 1-3, Higashi 1-chome, Yatabe-machi, Tsukuba-gun, Ibaragi-ken 305, Japan, and the deposit dates of strains, FERM-BP-53, BP-54, and BP-55 are Mar. 29, 1980, Aug. 29, 1980 and Aug. 29, 1980, respectively. These deposits were converted to deposits under the Budapest Treaty on Aug. 24, 1981 with FRI which has acquired the status of an Inernational Depository Authority as of May 1, 1981.

The culture medium utilized in the present invention for the production of MPA can be any known nutrient culture medium containing carbon sources, nitrogen sources, inorganic salts, and when required, minor nutrients. Suitable carbon for the medium include saccharides such as glucose, fructose and sucrose, and hydrolyzed starch. Suitable nitrogen sources include sodium nitrate, ammonium sulfate, and the like and amino acids such as glycine. Suitable inorganic salts include $K_2HPO_4$, $MgSO_4$, $FeSO_4$, $CuSO_4$, $ZnSO_4$, $K_2MoO_4$, $CaSO_4$ and the like.

Known nutrient culture media suitable for MPA production can also be preferably used such as those described by W. L. Muth et al, in *Antimicrob. Agents Chemotherap.*, 8, 321-327, 1975; and in British Patents 1,158,387 and 1,157,099.

Cultivation is carried out preferably under aerobic conditions at a pH of from 3 to 8 at a temperature ranging from 20° to 30° C. until a substantial amount of MPA has accumulated in the culture medium, for example, in about 6 to 14 days. The MPA which accumulates in the culture medium may be recovered by an entirely conventional method such as over an ion-exchange resin.

Having generally described the invention, a further understanding can be obtained by reference to certain specific examples which are provided herein for purposes of illustration only and are not intended to be limiting unless otherwise specified.

EXAMPLE 1

*Penicillium brevi-compactum* QM-8406 ATCC 16024 was cultured on a slant of Czapec-Dox agar medium at 27° C. for 10 days until conidia (spores) had fully formed on the grown mycelia. The conidia were scraped together and suspended in a sufficient amount of 0.05% sodium lauryl sulfate solution and the suspension was maintained at room temperature for 30 minutes. Thereafter, the conidia were collected by filtration asceptically over a cellulose membrane filter (Millipore Corp., Bedford, Mass. 01730: pore size 8.0 μm) and suspended in a 0.05 M phosphate buffer solution at pH 6.8 containing N-methyl-N'-nitro-N-nitrosoguanidine (NG) so that the suspension contained $10^5$-$10^6$/ml conidia and 1000 mcg/ml NG at the final concentration. Then, the suspension was maintained at 0° C. for 10 minutes. In this mutation treatment, approximately 99% of the cells were killed.

The conidia thus treated were washed with 0.05 M phosphate buffer solution at pH 6.8 and were inoculated on plates of a nutrient agar medium containing 1,500 mcg/ml clofibrat and having the composition given in Table 1.

TABLE 1

| Composition of medium (pH 6.5) | |
|---|---|
| ingredient | amount (%) |
| glucose | 3.0 |
| $NaNO_3$ | 0.3 |
| $NaHPO_4$ | 0.1 |
| $MgSO_4.7H_2O$ | 0.05 |
| KCL | 0.05 |
| $FeSO_4$ | 0.001 |
| agar | 1.5 |

The plates were then incubated at 25° C. until colonies formed on the plates. The colonies were picked-up and sustained on slants of the same nutrient agar medium shown in Table 1. By this procedure 54 clofibrat-resistant mutants were obtained.

In order to evaluate the productivity of MPA, the mutants were cultured in a culture medium having the composition shown in Table 2. Thereafter, *Penicillium brevi-compactum* AJ 117090 (FERM BP-53), which produced more MPA than the parent strain, was selected.

TABLE 2

| Composition of medium (pH 6.0) | | | |
|---|---|---|---|
| ingredient | amount | ingredient | amount |
| glucose | 10% | $FeSO_4$ | 2.0 ppm |
| glycine | 1.46% | $CuSO_4$ | 0.3 ppm |
| methionine | 0.05% | $ZnSO_4$ | 0.25 ppm |
| $MgSO_4.7H_2O$ | 0.1% | $MnSO_4$ | 0.16 ppm |
| $KH_2PO_4$ | 0.3% | $K_2MoO_4$ | 0.02 ppm |

In the same manner, *P. brevi-compactum* AJ 117094 resistant to clofibral and methylvialogen dye and *P. brevi-compactum* AJ 117096 (FERM BP-55) resistant to clofibrat and dodecatrimethyl ammonium chloride were induced from AJ 117090. In this procedure, the two mutant strains were grown in separate agar media each of the composition shown in Table 1, one of which contained 100 mcg/ml methylviologen dye and the other of which contained 25 mcg/ml dodecatrimethyl ammonium chloride.

Table 3 shows the resistance of these mutants to the chemicals.

TABLE 3

| | Resistance of the Mutants | | | |
|---|---|---|---|---|
| | | medium containing | | |
| Strain No. | no chemical | clofibrat 1,500 ppm | M V 100 ppm | ADAC 25 ppm |
| Q M 8404 (Parent) | +++ | − | − | − |
| AJ 117090 | +++ | ++ | − | − |
| AJ 117094 | + | ± | + | − |
| AJ 117096 | ++ | + | − | + |

+++: very abundant growth
++: abundant growth
+: moderate growth
±: poor growth
−: no growth In this experiment, the conidia of each mutant were cultured on plates of the agar medium of Table 1 supplemented with each chemical at 25° C. for 7 days, and the degree of growth was determined with the naked eye.

Paralleling this experiment, these mutants were evaluated for their MPA productivity. In order to do this fifty ml portions of the culture medium of the composition shown in Table 2 were placed into 500 ml flasks and heated at 120° C. for 10 minutes for sterilization. Each flask was supplimented with 1.0 g solid, separately sterilized CaCO$_3$. Strains of *Penicillium brevi-compactum*, AJ 117090, AJ 117094, and AJ 117096 which had been grown on the nutrient agar medium of the composition shown in Table 1 were inoculated into each batch of the culture medium in the flasks and were cultured at 27° C. with shaking for 6 days, or without shaking for 14 days, respectively. After the pH of each culture medium was adjusted at 10.5, insoluble residue such as mycelia were removed by filtration and the amount of MPA in the filtrate was determined by high performance liquid chromatography (Model 635, Hitachi, Ltd., Tokyo, equipped with a column of the cation exchange resin. Type Zipak SCX, and UV-detector at 24 nm), at 45° C. at a flow rate of 2 ml/min. using a 0.1 M phosphate buffer solution of pH 6.0 as the carrier fluid.

The results obtained are shown in Table 4.

TABLE 4

| | Amount of MPA accumulated (mg/dl) | |
|---|---|---|
| Strain No. | Cultivation with shaking | without shaking |
| QM 8404 (parent) | 130 | 170 |
| AJ 117090 (clofibrat$^r$) | 170 | 250 |
| AJ 117094 (clofibrat$^r$,MV$^r$) | 230 | 340 |
| AJ 117096 (clofibrat$^r$, DTAC$^r$) | 240 | 360 |

As shown in Table 4, the mutants of the present invention produced more MPA than each parent strain.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method for producing mycophenolic acid by fermentation, which comprises:
   (1) aerobically culturing in a culture medium under conditions suitable for the accumulation of said mycophenolic acid, a strain of Penicillium identified as *Penicillium brevicompactum* FERM BP-53, *Penicillium brevicompactum* FERM-BP-54, or *Penicillium brevicompactum* BP-55 which is capable of producing mycophenolic acid; and
   (2) recovering the mycophenolic acid which accumulates in the culture medium.

* * * * *